United States Patent [19]

Beers et al.

[11] Patent Number: 5,508,273
[45] Date of Patent: Apr. 16, 1996

[54] SUBSTITUTED PHOSPHONIC ACIDS AND DERIVATIVES USEFUL IN TREATING BONE WASTING DISEASES

[75] Inventors: Scott Beers; Elizabeth A. Malloy, both of Flemington; Charles Schwender, Califon, all of N.J.

[73] Assignee: Ortho Pharmaceutical Corporation, Raritan, N.J.

[21] Appl. No.: 176,354

[22] Filed: Dec. 30, 1993

[51] Int. Cl.⁶ .................... A61K 31/66; C07F 5/06; C07F 9/02
[52] U.S. Cl. ............ 514/141; 514/129; 514/145; 514/146; 514/148; 558/166; 558/178; 558/179; 558/180; 558/214; 568/8; 568/11
[58] Field of Search .................... 514/145, 146, 514/107, 141, 129, 131, 148; 568/8, 11; 558/166, 178, 179, 180, 214

[56] References Cited

U.S. PATENT DOCUMENTS 5,242,908 9/1993 Payman et al. .................... 514/107

FOREIGN PATENT DOCUMENTS 7114080 6/1965 Japan.

*Primary Examiner*—Theodore J. Criares
*Attorney, Agent, or Firm*—Ralph R. Palo

[57] ABSTRACT

Compounds represented by the formula I:

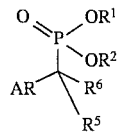

are disclosed as agents for use in treating bone wasting diseases.

19 Claims, No Drawings

SUBSTITUTED PHOSPHONIC ACIDS AND DERIVATIVES USEFUL IN TREATING BONE WASTING DISEASES

BACKGROUND OF THE INVENTION

Osteoporosis is a bone-wasting disease in which there is an imbalance or uncoupling between the rate of bone formation and resorption resulting in a decrease in total bone mass. As a result of this decrease in bone mass the skeleton becomes weakened and unable to bear the normal weight-bearing stresses. The effects of osteoporosis are generally seen in the weight-bearing part of the skeleton, especially the spine and hips, which can fracture in the absence of trauma. Osteoporosis affects about 24 million people in the United States and 200 million worldwide and is blamed for 2.5 million fractures a year in elderly women. The American Medical Association estimates that 25% of women will suffer fractures of the hip or spine in their lifetime as a result of osteoporosis.

The current therapies for postmenopausal osteoporosis consist of treatments which are for the most part preventative; estrogen replacement, bisphosphonates, vitamin D metabolites and calcium supplements act to inhibit bone resorption associated with the onset of menopause. Estrogen replacement in these patients is quite effective in reducing further loss of bone mass but it does not induce an increase in bone mass which is needed to reduce fracture risk and pain. These treatments have little utility in the treatment of those patients with existing osteoporosis-induced loss of bone mass who have a high fracture risk and back/joint pain. Postmenopausal women with vertebral bone mass of less than 100 mg/cc would be considered below the "fracture threshold" and would be candidates for treatment with an agent which would increase bone mass and thereby restore lost bone. The present invention focuses on agents which are useful in treating bone wasting diseases by increasing an individuals bone mass and thus reducing or eliminating fracture risk. The therapeutic need for this type of agent is clearly present, especially when one considers the poor patient compliance associated with estrogen replacement therapies.

The assignees of the present invention have filed a number of applications, Ser. Nos. 732,267, 111,677, 111,803 and 111,804, directed to certain novel benzylphosphonates. Such compounds were shown to have activity in treating bone wasting diseases. They are, however, structurally different from the compounds of the present invention.

SUMMARY OF THE INVENTION

Accordingly, the present invention is directed to substituted aralkylphosphonate compounds represented by the general formula I:

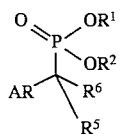

wherein $R^1$, $R^2$, AR, $R^5$ and $R^6$ are defined hereinafter and have been found to have utility in treating bone wasting diseases including osteoporosis. The invention is also directed to pharmaceutical compositions containing the compounds of formula I and methods of treatment of such bone wasting diseases.

DETAILED DESCRIPTION OF THE INVENTION

The present invention is directed to compounds represented by the formula I:

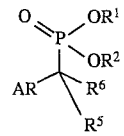

wherein $R^1$ and $R^2$ are the same or different and selected from any of H, $C_1$-$C_4$ alkyl, $C_1$-$C_4$ alkylsulfonyl, $C_1$-$C_4$ alkylNR$^3$R$^4$ wherein $R^3$ and $R^4$ are the same or different and are selected from either H or $C_1$-$C_4$ alkyl, aralkyl wherein the alkyl portion has 1 carbon atom, and the aryl portion is optionally independently substituted with any of halo, nitro, $C_1$-$C_2$ or alkyl or methylsulfonyl. Most preferably, $R^1$ and $R^2$ are both H. Compounds wherein either or both of $R^1$ and $R^2$ are other than H are generally less active than their corresponding acids and thus may be useful as intermediates in making the acid or as prodrugs.

AR is aryl where aryl is phenyl or naphthyl or substituted aryl wherein the substituents are independently selected from any of $C_1$-$C_4$ alkoxy, $C_1$-$C_8$ alkyl, cyano, halo, hydroxy, nitro, phenoxy, phenyl, or trifluoromethyl. More preferably, AR is phenyl or naphthyl substituted by any of $C_1$-$C_4$ alkyl, halo, phenyl, nitro, or trifluromethyl. Preferably, there are 1 or 2 substituents and most preferably one substituent. Most preferably, AR is phenyl or naphthyl wherein the substituent is alkyl or trifluoromethyl.

$R^5$ is selected from any of carboxyl, carboalkoxy, $C_3$-$C_7$ cycloalkyl, aryl, COaryl, COalkyl, COcycloalkyl, or aralkyl such as $(CH_2)_n$-aryl where n=1–6, wherein the aryl portion may be optionally independently substituted with any of amino, acylamino such as acetamido and benzamido, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl, or trifluoromethyl. More preferably, $R^5$ is selected from any of aryl, phenyl, $C_3$-$C_7$ cycloakyl, or substituted aryl wherein the substituents are independently selected from any of $C_1$-$C_4$ alkoxy, $C_1$-$C_4$ alkyl, phenyl, or trifluoromethyl. Preferably, there are 1 or 2 substituents and most preferably 1 substituent.

$R^6$ is selected from any of hydrogen, carboxy, $C_1$-$C_4$ carboalkoxy, $C_3$-$C_7$ cycloalkyl, aryl, CO-aryl, COalkyl, COcycloalkyl, or aralkyl such as $(CH_2)_n$-aryl where n=1–6, wherein the aryl portion may be optionally independently substituted with any of amino, acylamino such as acetamido and benzamido, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl, or trifluoromethyl. More preferably, $R^6$ is selected from any of aryl, phenyl, $C_3$-$C_7$ cycloakyl, or substituted aryl wherein the substituents are independently selected from any of $C_1$-$C_4$ alkoxy, $C_1$-$C_4$ alkyl, phenyl, or trifluoromethyl. Preferably, there are 1 or 2 substituents and most preferably 1 substituent. Most preferably, $R^6$ is H.

The following compounds are, however, not included within the scope of the present invention:
a) $R^1R^2$ are alkyl, AR is phenyl or phenyl substituted by halo,alkoxy,alkyl, trifluoromethyl, $R^5$ is carboxyl, phenyl, 1-naphthyl, substituted phenyl, 1-(4-$NO_2$)-naphthyl, cyclopentyl or cyclohexyl, $(CH2)_n$Aryl where aryl is phenyl and n=1,2, and $R^6$=hydrogen.

b) $R^1R^2$ is hydrogen, AR is phenyl, $R^5$ is carboxyl, phenyl or (CH2)nAryl where Aryl is phenyl and n=1 or 2, and $R^6$ is hydrogen.

As used herein, unless otherwise noted alkyl and alkoxy whether used alone or as part of a substituent group, include straight and branched chains of 1–4 carbon atoms. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl, 2-methylpentyl. Alkoxy radicals are oxygen ethers formed from the previously described straight or branched chain alkyl groups.

The term "aryl" as used herein alone or in combination with other terms indicates aromatic hydrocarbon groups such as phenyl or naphthyl. The term "aralkyl" means an alkyl group substituted with an aryl group. The term "independently" means that there can be one or more substituents and when there are more than one they can be the same or different.

The invention definition of formula I includes racemates, individual enantiomers, and diastereomers as caused by the presence of stereogenic carbon or phosphorous atoms.

Representative salts of the compounds of formula I which may be used include pharmaceutically acceptable basic salts made from organic and inorganic bases such as ammonium, cyclohexylammonium, tris-ethanolammonium, arginine and lysine. Such salts can be made by reacting the phosphonic acids of formula I with the appropriate agent and recovering the salt.

Particularly preferred compounds of the present invention include:

2-Trifluoromethylphenyl(phenyl)methylphosphonic acid (CP#16);

O,O-Diethyl 2,5-dimethylphenyl(phenyl)methylphosphonate (CP#79);

2,5-Dimethylphenyl(phenyl)methylphosphonic acid (CP#19);

O,O-Diethyl 3-Trifluoromethylphenyl(3-trifluoromethylphenyl)-methylphosphonate (CP#83);

3-Trifluoromethylphenyl(3-trifluoromethylphenyl)methylphosphonic acid (CP#20);

O,O-Diethyl 3-Trifluoromethylphenyl(3-trifluoromethylbenzyl)methylphosphonate (CP#57);

3-Trifluoromethylphenyl(3-trifluoromethylbenzyl)methylphosphonic acid (CP#35);

O,O-Diethyl 4-Chlorobenzyl(1-naphthyl)methylphosphonate (CP#61);

4-Chlorobenzyl(1-naphthyl)methylphosphonic acid (CP#48);

bis(4-Chlorobenzyl)(1-naphthyl)methylphosphonic acid (CP#49);

bisBenzoyl(1-naphthyl)methylphosphonic acid (CP#55);

O,O-Diethyl Benzoyl(1-naphthyl)methylphosphonate (CP#94); and

Benzoyl(1-naphthyl)methylphosphonic acid (CP#51).

The compounds of formula I are listed in Table 1 as examples of the invention and may be prepared according to the following reaction schemes.

SCHEME I

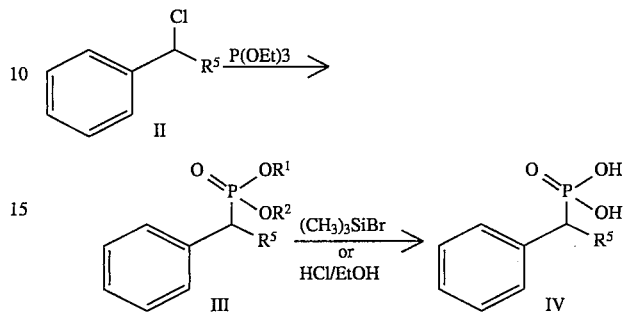

As shown in Scheme I, the substituted benzhydryl chloride or bromide, II prepared if necessary from the precursor alcohol or ketone, by reduction with a metal hydride such as $NaBH_4$ or $LiAlH_4$ and halogenation using reagents such as thionyl chloride or phosphorous tribromide, is reacted with trialkyl phosphite under temperatures of about 50°–200° C. to give an alkyl substituted-diphenylmethylphosphonate ester, III.

The free phosphonic acid, IV, is generated from the ester, III, by acidic hydrolysis using a concentrated hydrochloric acid/alcohol (2:1, 1:1, or 1:2) mixtures and refluxing temperatures for about 4–72 hours. Upon cooling the reaction mixture and concentration in volume, the crystalline acid product precipitated and was collected by filtration. This product may be recrystallized, if necessary, with solvents such as alcohols, alcohol-water, aqueous hydrochloric acid/ethanol mixtures, water, or acetic acid to give the purified product. Alternatively, the esters may be hydrolyzed using 4–12 equivalents of bromotrimethylsilane in excess methylene chloride or acetonitrile as solvent and stirring the mixture at about room temperature for about 10 minutes to 48 hours. The reaction mixture is evaporated/n vacuo to a residue which is crystallized by trituration with an alcohol, alcohol-water, acetic acid, acetic acid/ethanol, or hydrochloric acid. The residue obtained is dissolved in an alcohol and excess propylene oxide is added. Heating at 40°–100° C. for 1–2 hours gives the solid acid which is purified by recrystallization as above.

SCHEME II

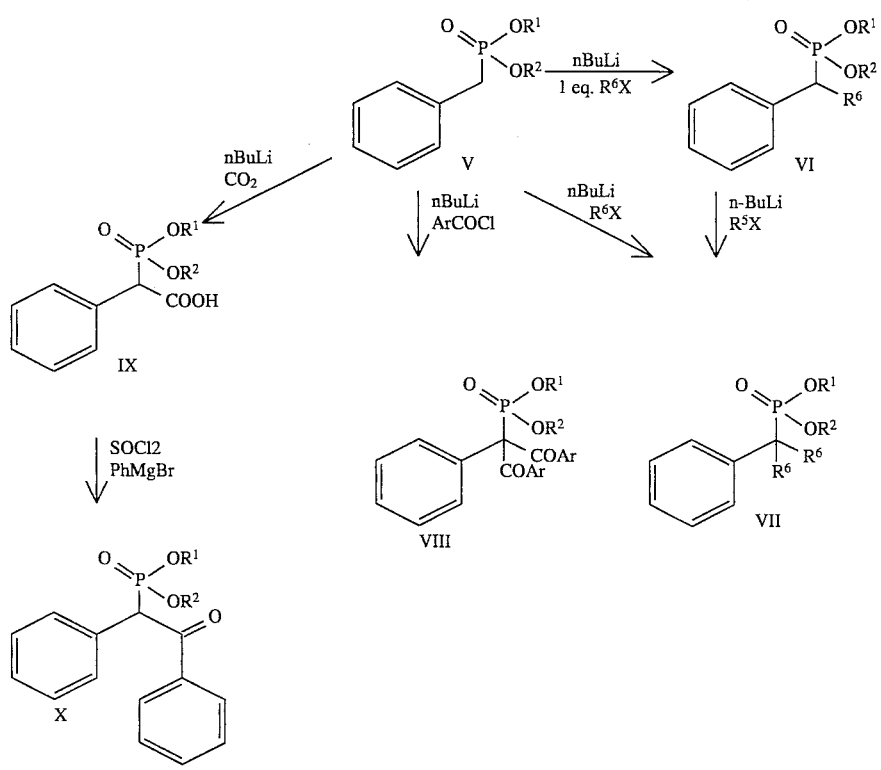

Introduction of $R^5$ and $R^6$ functionalization can be accomplished according to Scheme II by reacting intermediate dialkyl substituted-benzylphosphonates, V, with a base such as n-butyllithium, lithium diisopropylamide, or sodium hydride in an aprotic solvent such as tetrahydrofuran or diethyl ether at temperatures from −78° C. to 0° C. Addition of 1–2 equivalents of an appropriately substituted aralkyl halide to the reaction mixture and stirring for 1–24 hours at ambient temperature gave, upon hydrolytic workup, high yields of the mono alkylated benzylphosphonates, VI. Addition of excess aralkyl halide, 8–10 equivalents, to the mixture of base and dialkyl benzylphosphonate, V, yields the dialkylated benzylphosphonate ester, VII. Similarly, excess aroyl halide such as benzoyl chloride, affords the diacylated product, VIII. The synthesis of the mono acylated product, X, is achieved in high yield from the intermediate α-carboxyl, IX, obtained from V by reaction with n-butyllithium and carbon dioxide. Intermediate IX is converted to its acid chloride with oxalyl chloride or thionyl chloride which is then reacted with a reagent such as phenylmagnesium halide in tetrahydrofuran or diethyl ether at low temperatures such as −78° C. to give the mono acyl product, X. In examples where $R^5$ and $R^6$ are not identical, intermediate mono alkylated, VI, or mono acylated X, can be alkylated or acylated a second time as in the preparation of VII, and VIII. Acidic hydrolysis of the phosphonate esters as in Scheme I above gives the free phosphonic acids.

In all cases of this invention, the carbon directly attached to the phosphorous can exist in either the R or S configuration or as a mixture of both. The phosphonic acids, which are mixtures of stereochemical configuration at this center can be resolved by salt formation with chiral amines such as the ephedrines, methylbenzylamine, amino acids or derivatives including arginine and lysine, and basic alkaloids such as quinidine and brucine can be used to form salts with the enantiomeric mixtures of the phosphonic acid. The resulting diastereomeric salts can then be separated using normal methods such as differential dissolution or fractional crystallization.

Compounds of the present invention have utility to treat bone wasting diseases including osteoporosis in animals including humans through enhancement of bone calcification as well as inhibition of bone degeneration or resorption. The compounds of the present invention have been evaluated as inhibitors of human prostatic tyrosyl phosphatase, an isoenzyme similar to a tyrosyl phosphatase present in human osteoblasts. Inhibitors of the enzyme are involved with the stimulation of osteoblast cell proliferation in cell culture which is predictive of enhancement of bone mass and bone formation in vivo. Inhibitors of osteoclastic acid phosphatase prevent the resorptive action of osteoclasts and thereby prevent the degradation of bone mass associated with osteoporosis. Table 1 reports the results of the compounds of the present invention in inhibiting human prostatic tyrosyl phosphatase and osteoclastic acid phosphatase. Compounds of this invention are characterized by their $IC_{50}$ or concentration required to inhibit 50% of the enzyme reaction or the percent enzyme inhibition observed at 100 uM concentration. Their ability to stimulate osteoblast cell proliferation at 0.01 uM concentration is presented also in Table 1. Compounds wherein $R^1$ or $R^2$ are other than H are esters which to date have not demonstrated significant activity in the screens at concentrations used to test the acidic compounds of the present invention. However, such compounds may be useful as prodrugs to the acid ($R^1$ and $R^2$ equal H) and as intermediates useful in making the corresponding acid.

Tyrosyl Phosphatase Assay

Inhibition of the activity of tyrosyl protein phosphatase was evaluated by incubating an aliquot of purified human prostatic tyrosyl protein acid phosphatase (Sigma Chemical Co.) with radiolabeled phosphotyrosine. The radiolabeled substrate, ($^{14}$C)-phosphotyrosine, is separated from the product, ($^{14}$C)-tyrosine by ion exchange chromatography and the production of radiolabeled tyrosine is quantified. Test compounds are screened at a concentration of one micromolar to 1 nM. The ability of test compounds to inhibit tyrosyl phosphatase was expressed as the % inhibition at the highest concentration of test compound tested and/or as the $IC_{50}$ in Table 1.

The test compounds were incubated in the presence of tyrosyl acid phosphatase and radiolabeled substrate {($^{14}$C)-phosphotyrosine, (NEN Dupont Custom Synthesis)} plus cold O-phospho-L-tyrosine{(10 uM) (Sigma Chemical Co.)} in a 0.05 mM sodium acetate buffer (pH 5.5) for 30 minutes at 37° C. The reaction was stopped by placing the assay tubes on ice and with the addition of a 100 ul aliquot of a enzyme inhibitor solution (1.1 mM sodium orthovanadate, Sigma Chemical Co.; 0.55M sodium fluoride, Sigma Chemical Co.). The incubation mixture was passed over an ion-exchange column {(Ag 1-X8) (Bio-Rad Laboratories)} and washed with 2.5 ml of distilled, deionized water. The total column effluent containing the radiolabeled product ($^{14}$C-tyrosine) was collected and quantified by liquid scintillation spectroscopy. The test compounds $IC_{50}$ was calculated using a quantal (all-or-none) dose-response calculation.

Osteoclastic Acid Phosphatase (OAP)

Human osteoclastic acid phosphatase (OAP) is purified from hairy cell leukemia spleen, following the protocol outlined [J. J. Stepan, Biochemical and Biophysical Research Communications,165,1027–1034 (1989)]. The enzyme was stored at −80° C. and was diluted in 50 mM, pH 5.0, sodium acetate buffer prior to use. Test compounds were dissolved in ethanol, DMSO, or water and tested at 100 μM. The assay measures the ability of the enzyme to dephosphorylate methylumbelliferone phosphate to the product, methylumbelliferone, which is fluorescent. The enzyme assay is performed in 50 mM, pH 5.0, sodium acetate buffer as follows: 5 μL of compound was added to 150 μL Of buffered enzyme solution. The reaction was initiated by addition of 50 μL of the buffered solution (0.1 mM) of methylumbelliferyl phosphate, making the final substrate concentration equal to 25 μM. The reaction was performed at room temperature at pH=5.0 and terminated after 20 minutes by the addition of 50 μL of 4N NaOH. The reaction product, methylumbelliferone, was measured by fluorescence determination using a Dynatech Microfluor Fluorescence detector. The test compounds were screened at 100 μM in aqueous buffer containing ethanol or DMSO to enhance their solubility and compared with the control enzyme activity. Activity as an inhibitor of the enzymatic reaction is expressed as the % inhibition at the screening concentration (100 μM), or the $IC_{50}$ (μM) defined as the concentration of inhibitor required to inhibit 50% of the dephosphorylation reaction.

Osteoblast cell proliferation

The action of select compounds to stimulate osteoblast growth can be measured in culture by estimating the rate of DNA synthesis by the rate of $^3$H-thymidine incorporation into DNA. Only cells undergoing mitosis will synthesize new DNA and thus only these cells will incorporate the radiolabeled DNA-specific thymidine. The stimulation of the proliferation and differentiation of bone-forming cells, osteoblasts, is a prerequisite for an increase in bone formation and bone mass. The ability of agents to increase osteoblast proliferation and differentiation can be predicted by their action on cultured osteoblast-line cells in vitro. In this test, mouse (MC3T3-E 1) cloned by Sudo et al. Koriyama, Japan) and human (TE-85) osteoblast-line cells (American Type Tissue Culture Collection, #CRL 1543, Rockville, Md.) were cultured/n vitro and the effect of various agents was tested on osteoblast cell proliferation. Osteoblasts were isolated and cultured according to literature methods. [J. E. Puzas, R. H. Drivdahl, A. G. Howard, and D. J. Baylink, *Proc. Soc. Exper. Biol. Med.*, 166 113–122, 1091]. Cells were harvested from large culture flasks, where they were allowed to grow to near confluency, using trypsin. The cells were plated into 96 well culture plates, 1600 cells in 100 μL per well in Dulbecco's Modified Eagle's Medium with 25 mM HEPES buffer, L-glutamine (584 mg/L); D-glucose (4.5 g/L) supplemented with fetal bovine sera (10%); penicillin (100 units/mL)and streptomycin (100 mcg/mL); sodium pyruvate (10 μM final concentration). The cells were allowed to plate overnight in DMEM containing 10% fetal bovine sera at 37° C., in an atmosphere of 5% $CO_2$/95% air. Following their placement into 96 well culture plates all the osteoblast-line cells, either the MC3T3-E 1 or the TE-85 cell lines, were allowed an additional 24 hours preincubation period in media containing only 0.1% fetal bovine sera. The next day the test compounds were added and screened at concentrations ranging from $10^{-4}$ to $10^{-8}$M depending on the study. Twenty hours later, a 20 μL aliquot of media containing 0.4 μCi of $^3$H-thymidine was added to each culture well. The cells were then incubated an additional 4 hours. The incubation was terminated by aspirating the media and washing with HBSS (Hank's Balanced Salt Solution). The cells were then treated with 100 μL of 0.5% trypsin and 5.3 mm of EDTA for 30 minutes at room temperature. The cells were then aspirated onto a glass fiber filter and washed with water. The radioactivity on the filters was quantified by liquid scintillation spectroscopy. The rate of $^3$H-thymidine incorporation into DNA is then utilized as an index of cell proliferation. The results are shown in Table 1 expressed as % times control where control is 100%.

TABLE 1

BIOLOGICAL ACTIVITIES

| Cmpd | Tyr-Pase IC50 uM | OAPase % Inh@100 uM | OAPase IC50 uM | Osteoblast Prolif (% XControl@ 0.01 uM) |
|---|---|---|---|---|
| 4 | 6.9 | — | 1.4 uM | |
| 5 | 23.5 | 6 | — | |
| 6 | 37 | 40 | — | |
| 7 | — | 16 | — | |
| 8 | — | 16 | — | |
| 9 | 13.75 | 30 | — | |
| 10 | 17.4 | — | 100 uM | 124 |
| 11 | 37.8 | 13 | — | |
| 12 | 40.9 | 12 | — | 124.4 |
| 13 | 30.7 | 12 | — | |
| 14 | 8.9 | 9 | — | |
| 15 | 15 | 31 | — | |
| 16 | 67.1 | 26 | — | |
| 17 | 17 | 89 | — | |
| 18 | 14 | 4 | — | |
| 19 | 36.5 | 13 | — | |
| 20 | 29.3 | 28 | — | |
| 21 | 44.2 | 10 | — | |
| 22 | 152 | 22 | — | 116 |

TABLE 1-continued

BIOLOGICAL ACTIVITIES

| Cmpd | Tyr-Pase IC50 uM | OAPase % Inh@100 uM | OAPase IC50 uM | Osteoblast Prolif (% XControl@ 0.01 uM) |
|---|---|---|---|---|
| 23 | 40.8 | — | 100 uM | |
| 24 | 36.6 | 28 | — | |
| 25 | 15.7 | 94 | 29 uM | |
| 26 | 101.8 | 20 | — | |
| 27 | 142.5 | 17 | — | |
| 28 | 50–100 | 100 | 17 uM | |
| 29 | 290 | 15 | — | 99 |
| 30 | 81.9 | — | — | 97 |
| 31 | 36 | 25 | — | |
| 32 | 66.2 | 10 | — | |
| 33 | 34.5 | 30 | — | 104 |
| 34 | 89.2 | 15 | — | 156 |
| 35 | 9 | — | 100 uM | |
| 36 | 100 | 12 | — | |
| 37 | 30.6 | 25 | — | |
| 38 | 35.7 | 100 | 22 uM | |
| 40 | >1 uM | 19 | — | |
| 41 | >1 uM | 81 | 11 uM | |
| 42 | >1 uM | 100 | 6.3 uM | |
| 43 | >10 uM | 73 | 11.4 uM | |
| 44 | — | 73 | — | — |
| 45 | 67.2 | 92 | 21 uM | |
| 46 | — | 75 | — | |
| 47 | — | 80 | — | |
| 48 | 56.9 | 94 | 21 uM | |
| 49 | >1 uM | 87 | 9.29 uM | |
| 50 | — | — | — | |
| 51 | — | — | — | |
| 52 | — | — | — | |
| 53 | — | 95 | 5.94 uM | |
| 54 | — | — | — | |
| 55 | >1 uM | 96 | 1.4 uM | |

To prepare the pharmaceutical compositions of this invention, a compound of formula I, as the active ingredient is mixed with a pharmaceutical carrier according to conventional pharmaceutical compounding techniques, which carrier may take a wide variety of forms depending on the form of preparation desired for administration, e.g.; oral, by suppositories, injectable, or parenteral. In preparing the compositions in oral dosage form, any of the usual pharmaceutical media may be employed. Thus, for liquid oral preparations, such as, for example; suspensions, elixirs and solutions, suitable carriers and additives include water, glycols, oil, alcohols, flavorants, preservatives, coloring agents and the like. For solid oral preparations such as, for example; powders, capsules and tablets, suitable carriers and additives include, starches, sugars, diluents, granulating agents, lubricants, binders, disintegrating agents, and the like. Because of their ease of administration, tablets and capsules represent the most advantageous oral dosage unit form in which case, solid pharmaceutical carriers are obviously employed. If desired, tablets may be sugar coated or enteric coated by standard techniques. For suppositories, the carrier will usually comprise cocoa butter. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per unit dosage unit, e.g., tablet, capsule, powder, injection, suppository, teaspoonful and the like, from about 0.001 mg to 50 mg/kg. The use of either daily administration or post-periodic dosing may be employed.

EXAMPLES

The following examples describe the invention in greater detail and are intended to illustrate the invention but not to limit it. All examples given have been characterized by 300 MHz $^1$H NMR (reported as ppm downfield from tetramethylsilane) and by Mass Spectra (DCI) evaluation.

Each compound has satisfactory C,H,N elemental analysis within ±0.4% of theoretical values. Unless noted, starting materials used in the examples were obtained from commercial sources, synthesized using cited literature methodology, or, if new, described as an example in the invention. Examples 1–3 describe the preparation of intermediates useful in preparing compounds of the present invention. The Example section contains written Examples and Table 2, which contains additional Examples. The additional Examples reference a fully written Example (the column headed "EXP") for the purpose of describing the general method used to make that compound; e.g.; in Table 2 CP#13 was made by the same procedures used to make the compound in the written Example 4.

EXAMPLE 1

O,O-Diethyl 3-Trifluoromethylphenylmethylphosphonate

3-Trifluoromethylbenzylchloride (50 g, 257 mmol) and triethyl phosphite (53.4 g, 321 mmol) were combined, under $N_2$, and heated to 160° C. for 18 hours. The reaction mixture was distillated at 105°–110° C. to give 69.5 g (91.3%) of analytically pure product as a colorless oil. 300 MHz $^1$H NMR (CDCl$_3$): δ, 3.20 (d,2H, J=21.78 Hz, PCH2). MS: 297 (M+1).

EXAMPLE 2

2-(Trifluoromethyl)benzhydrol

To a solution of 2-(trifluoromethyl)benzophenone (20.0 g, 79.9 mmol) in ethanol (160 mL), under $N_2$, and cooled in an ice-$H_2O$ bath, was slowly added, in portions, NaBH$_4$ (9.07 g, 240 mmol). The slurry was stirred at room temperature for 64 hours. The reaction mixture was cooled to 0° C. and 1N. HCl was added until the mixture was of neutral pH. The mixture was extracted with $CH_2Cl_2$ (2×250 mL). The CHCl$_2$ extracts were combined, washed with $H_2O$ (2×100 mL), saturated aqueous NaCl (1×100 mL), dried (Na$_2$SO$_4$), filtered, and concentrated to dryness to give a quantitative yield of product as a pale yellow oil. 300 MHz $^1$H NMR (CDCl$_3$): δ, 6.32 (d,1H, J=3.48 Hz, (Ph)$_2$CH. MS: 252 (M$^+$), 235 (MH$^+$-H$_2$O).

EXAMPLE 3

2-(Trifluoromethyl)benzhydryl bromide 2-(Trifluoromethyl)benzhydrol (20.2 g, 79.9 mmol) was dissolved in ethyl ether (195 mL), and cooled in an ice-$H_2O$ bath, under $N_2$. To the resulting solution was added, dropwise, a solution of PBr$_3$ (3.80 mL, 40.0 mmol) in ethyl ether (95 mL). After addition was complete, the reaction mixture was brought to room temperature and stirred for 16 hours. The reaction mixture was cooled in an ice-$H_2O$ bath and quenched with $H_2O$ (200 mL). The aqueous layer was extracted with ethyl ether (2×200 mL). The combined organic extracts were dried (MgSO$_4$), filtered, and concentrated to dryness at low heat to give a quantitative yield of product bromide as a pale yellow oil. 300 MHz $^1$H NMR (CDCl$_3$): δ6.69 (s, 1H, (Ph)$_2$CH. MS: 235 (M$^+$-Br).

EXAMPLE 4 (CP#14)

2-Trifluoromethylphenyl(phenyl)methylphosphonic Acid

A solution of 2-(trifluoromethyl)benzhydryl bromide (25.2 g, 79.8 mmol) in triethyl phosphite (20.5 mL, 120 mmol), under $N_2$, was heated at 155° C. for 16 hours. Excess triethyl phosphite was removed by distillation to give a yellow oil, 28.8 g. The crude product was chromatographed on a silica gel column. Elution with ethyl acetate/hexane (1:1) afforded analytically pure O,O-diethyl 2-trifluoromethylphenyl(phenyl)methylphosphonate as a pale yellow oil. 300 MHz $^1$H NMR ($CDCl_3$): δ4.86 (d, 1H, J=26.18 Hz, PCH). MS: 373 (M+1).

O,O-Diethyl 2-trifluoromethylphenyl(phenyl)methylphosphonate (490 mg, 1.32 mmol) was dissolved in ethanol (26 mL) and 20 mL of concentrated hydrochloric acid. The reaction mixture was heated at 110° C. for 24 hours and then concentrated to dryness to give a pale yellow gum, 380 mg. The gum was washed with hexane giving 174 mg (43%) of analytically pure acid as a white solid, mp 127°–130° C. 300 MHz $^1$H NMR ($CDCl_3$): δ4.81 (d,1H, J=26.1 Hz, PCH). MS: 317 (M+1).

EXAMPLE 5 (CP#79)

O,O-Diethyl 2,5-dimethylphenyl(phenyl)methylphosphonate

A solution of 2,5-dimethylbenzhydryl bromide (64.2 g, 233 mmol) prepared according to Example 3, was heated at 155° C., under $N_2$, in triethyl phosphite (60.0 mL, 350 mmol), for 16 hours. The excess triethyl phosphite was removed by distillation to give 76.6 g of a pale yellow oil. The crude product was chromatographed on a silica gel column. Elution with ethyl acetate/hexane (1:1) afforded analytically pure product as a pale yellow oil, 57.36 g (74.0%). 300 MHz $^1$H NMR (CDCl3): δ, 4.64 (d,1H, J=26.0 Hz, PCH), 2.33 (s, 3H, $PhCH_3$), 2.28 (s, 3H, $PhCH_3$). MS: 333 (M+1).

EXAMPLE 6 (CP#19)

2,5-Dimethylphenyl(phenyl)methylphosphonic Acid

O,O-Diethyl 2,5-dimethylphenyl(phenyl)methylphosphonate (15.0 g, 45.1 mmol) was dissolved in ethanol (172 mL) and concentrated hydrochloric acid (290 mL). The resulting solution was heated at 110° C. for 52 hours. The mixture was cooled and the solid which formed was collected by filtration, washed with $H_2O$(2×50 mL), $CH_2Cl_2$ (3×30 mL), and dried to afford 11.0 g (88.6 %) of analytically pure product as a white solid, mp 204°–207° C. 300 MHz $^1$H NMR (DMSO-D): δ,4.44 (d,1H, J=24.8 Hz, PCH), 2.25 (s, 3H, $PhCH_3$), 2.20 (s, 3H, $PhCH_3$). MS: 277 (M+1).

EXAMPLE 7 (CP#83)

O,O-Diethyl bis(3-trifluoromethylphenyl)methylphosphonate

A solution containing 3,3'-bis(trifluoromethyl)benzhydryl bromide (29.8 g, 77.6 mmol), prepared according to methods in Example 3 and triethyl phosphite (21.6 mL, 126 mmol), was heated at 155°–160° C. for 16 hours, under $N_2$. The reaction mixture was cooled and washed with $H_2O$ (2×150 mL) to remove the excess triethyl phosphite. The non-aqueous portion was added to $CH_2Cl_2$ (150 mL), dried ($MgSO_4$), filtered, and concentrated in volume to give a pale yellow oil, 30.1 g. The crude product was chromatographed on a silica gel column. Elution with ethyl acetate/hexane (1:1) afforded analytically pure product as a white solid, 10.7 g, (31.2%), mp 82°–85° C. 300MHz $^1$H NMR ($CDCl_3$): δ,4.54 (d,1H, J=25.3 Hz, PCH). MS: 441 (M+1).

EXAMPLE 8 (CP#20)

bis(3-Trifluoromethylphenyl)methylphosphonic Acid

O,O-Diethyl bis(3-trifluoromethylphenyl)methylphosphonate (6.12 g, 13.9 mmol) was dissolved in ethanol (220 mL) and 118 mL of concentrated hydrochloric acid. The resulting solution was heated at 95° C. for 66 hours. The mixture was concentrated in volume and a precipitate formed. The solid was filtered, washed with $H_2O$ (3×20 mL), and dried to give 3.60 g (67.4%)of analytically pure product as a white solid, mp 191°–193° C. 300 MHz $^1$H NMR (DMSO-$d_6$): δ,4.78 (d,1H, J=23.4 Hz, PCH). MS: 385 (M+1).

EXAMPLE 9 (CP#57)

O,O-Diethyl 3-Trifluoromethylphenyl(3-trifluoromethylbenzyl)methylphosphonate

A solution of O,O-diethyl 3-trifluoromethylbenzylphosphonate (20.0 g, 67.5 mmol) in tetrahydrofuran (90 mL) was cooled to −70° C. (dry ice bath), under $N_2$, and a solution of butyllithium (1.6M, in hexanes, 46.4 mL, 74.3 mmol) in 90 mL of dry tetrahydrofuran cooled to −70° C. (dry ice) was added. After 15 minutes, a solution of 3-trifluoromethylbenzylbromide (10.3 mL, 67.5 mmol)in tetrahydrofuran (90 mL) was added. The green reaction mixture turned yellow and was brought to room temperature and allowed to stir for 4 hours. The mixture was then quenched with $H_2O$ (200 mL), and extracted with ether (2×200 mL). The combined ether extracts were dried ($MgSO_4$), filtered, and concentrated to dryness to give a yellow oil, 32.3 g. The crude product was chromatographed on a silica gel column. Elution with ethyl acetate/hexane (1:1) afforded analytically pure product as a pale yellow oil, 24.1 g (78.4%). 300 MHz $^1$H NMR ($CDCl_3$): δ, 3.16–4.20 (m,7H, PCH, $PhCH_2$, 2($OCH_2$). MS: 455 (M+1).

EXAMPLE 10 (CP#35)

3-Trifluoromethylphenyl(3-trifluoromethylbenzyl)methylphosphonic Acid

O,O-Diethyl 3-trifluoromethylphenyl(3-trifiuoromethylbenzyl)methylphosphonate (20.1 g, 44.2 mmol) was dissolved in ethanol (50 mL), 1-butanol (250 mL) and 300 mL of concentrated hydrochloric acid. The resulting mixture was heated at 110° C. for 68 hours. Upon cooling, an oil separated. The mixture was concentrated to dryness, and the residue was redissolved in $CH_2Cl_2$ (200 mL). The $CH_2Cl_2$ was dried ($NaSO_4$), filtered, and concentrated to dryness to afford 12.4 g (70.8%) analytically pure product as a white solid, mp 88°–90° C. 300 MHz $^1$H NMR (DMSO-D): δ, 3.10–3.60 (m,3H, PCH, $PhCH_2$). MS: 399 (M+1).

EXAMPLE 11 (CP#48)

4-Chlorophenyl(1-naphthyl)methylphosphonic Acid

Tetrahydrofuran (40 mL) was placed in a 500 mL 3-necked flask, under $N_2$, and was cooled to −78° C. in a dry ice-acetone bath. To this was added butyllithium (1.6M solution in hexanes, 31.4 mL, 50.3 mmol). To the resulting solution was added a solution of O,O-diethyl 1-naphthylmethylphosphonate (10.0 g, 35.9 mmol) in tetrahydrofuran (50 mL). The reaction mixture turned deep yellow. After 15 minutes, a solution of 4-chlorobenzyl chloride (5.79 g, 35.9 mmol) in THF (50 mL) was added. The reaction mixture was allowed to stir at 17°–18° C. for one hour and then quenched with $H_2O$ (100 mL) and extracted with ethyl ether (2×150 mL). The combined ether extracts were dried ($MgSO_4$), filtered, and concentrated to dryness to give a yellow oil, 15.4 g. The crude O,O-diethyl 4-chlorobenzyl(1-naphthyl)methylphosphonate was chromatographed on a silica gel column. Elution with EtOAc/hexane (1:1) afforded pure ester as a pale yellow oil, 13.2 g (90.9%). 300 MHz $^1$H NMR ($CDCl_3$): δ4.20–4.40 (m,1H, PCH). MS: 403 (M+1).

A solution of O,O-diethyl 4-chlorobenzyl(1-naphthyl)methylphosphonate (13.2 g, 32.7 mmol)in $CH_2Cl_2$ (225 mL), under $N_2$, was treated with bromotrimethylsilane (25.9 mL, 196 mmol) and the resulting yellow solution was stirred at room temperature for 16 hours. The reaction mixture was concentrated to dryness and the residue obtained was triturated with $H_2O$ (100 mL) and methanol (150 mL) and stirred at room temperature for 3.5 hours. Addition of $H_2O$ (650 mL) produced a white solid which was filtered, washed with $H_2O$ (2×75 mL) and dried to give 11.8 g of a white solid which was dissolved in HCl (conc.,75 mL) and ethanol (100 mL) and was heated at 100° C. for one hour. The pale yellow solution was concentrated to ½ volume. Cooling yielded a solid which was filtered, washed with $H_2O$ (3×50 mL), and dried to afford 7.95 g, (70.2%) analytically pure product as a white solid, mp 204°–206° C. 300 MHz $^1$H NMR (DMSO-$d_6$): δ4.15–4.40 (m,1H, PCH), 3.20–3.64 (m,2H, p-Cl-$PhCH_2$). MS: 347 (M+1).

EXAMPLE 12 (CP#49)

bis(4-Chlorobenzyl)(1-Naphthyl)methylphosphonic Acid

To butyllithium (1.6M solution in hexanes, 120 mL, 194 mmol) and tetrahydrofuran (26 mL) cooled to −78° C., was added O,O-diethyl 1-naphthylmethylphosphonate (6.42 g, 23.1 mmol) in tetrahydrofuran (32 mL). After 15 minutes, a solution of 4-chlorobenzyl chloride (33.6 g, 208 mmol)in tetrahydrofuran (92 mL) was added. The dry ice bath was removed and the reaction mixture was allowed to warm to room temperature and stirred for 20 hours. The reaction mixture was quenched with $H_2O$ (200 mL) and extracted with ethyl ether (3×150 mL). The combined ether extracts were dried ($MgSO_4$), filtered, and concentrated to dryness to give a yellow oil, 37.4 g. The crude product was chromatographed on a silica gel column. Elution with ethyl acetate/hexane (1:1) afforded pure ester, diethyl bis(4-chlorobenzyl)(1-naphthyl)methylphosphonate as a pale yellow oil, 7.51 g (61.7%). 300 MHz $^1$H NMR ($CDCl_3$): δ[3.55–4.00 (m,8H, 2($OCH_2$), 2 (p-Cl-$PhCH_2$)]. MS: 527 (M+1).

A solution of diethyl bis(4-chlorobenzyl)(1-naphthyl)methyl phosphonate (7.51 g, 14.2 mmol) in $CH_2Cl_2$ (50 mL), under $N_2$, was treated with bromotdmethylsilane (11.3 mL, 13.1 g, 85.4 mmol) and the resulting yellow solution was stirred at room temperature for 16 hours. The solution was concentrated to dryness and the residue obtained was treated with concentrated hydrochloric acid (41 mL) and ethanol (155 mL) and heated at 100° C. for 1 hour. The reaction mixture was evaporated to dryness, and the residue was dissolved in $H_2O$ (60mL)/ethanol (180 mL). Addition of $H_2O$ (500 mL) yielded a tacky solid which was filtered and dried to afford 5.59 g (83.3%) analytically pure acid as an off-white solid, mp 142°–145° C. 300 MHz $^1$H NMR (TFA-D): δ4.08 (d,4H, J=16.44 Hz, 2(p-Cl-$PhCH_2$). MS: 471 (M+1).

EXAMPLE 13 (CP#55)

bis(Benzoyl)(1-naphthyl)methylphosphonic Acid.

O,O-Diethyl 1-naphthylmethylphosphonate (4.86 g, 18.0 mmol) was dissolved in anhydrous tetrahydrofuran (40 mL). To this solution cooled to −78° C. under nitrogen was added n-butyllithium (22 mmol). The mixture was allowed to stir for 20 minutes and benzoyl chloride (2.60 mL, 22.0 mmol) was added. The reaction mixture was allowed to warm to room temperature and stirred for an additional 45 minutes before it was quenched with aqueous ammonium chloride and extracted with ethyl acetate. The organic layer was dried over sodium sulfate, and evaporated to a residual oil which was purified by silica gel column chromatography eluting with ethyl acetate-hexane, 1:1. The desired ester was obtained as an oil. 300 MHz $^1$H NMR ($CDCl_3$): δ, 8.2–6.9 (m,17H, ArH), 3.75 (M, 4H,$CH_2$). MS: 487 (M+1), 383 (M-benzoyl).

The ester, O,O-diethyl bis(benzoyl)(1-naphthyl)methylphosphonate, (4.62 g, 9.51 mmol) was dissolved in methylene chloride (40 mL). Bromotrimethylsilane (5.00mL, 38.0 mmol) was added and the resultant mixture was stirred under nitrogen at room temperature for three hours. The mixture was evaporated, and the residue obtained was dissolved in ethyl acetate (100 mL), washed with water (2×50 mL), and dried over sodium sulfate. Evaporation of the organics gave a crude solid which was recrystallized from ethanol-water and then methanol-ether to give 2.55 g of an analytical sample of the acid, mp 153°–155° C. MS (DCl): 429 (M−1).

EXAMPLE 14 (CP#59)

O,O-Diethylphosphono-1-naphthylacetic Acid

O,O-Diethyl 1-naphthylmethylphosphonate (3.00 g,11.3 mmol) was dissolved in 75 mL of tetrahydrofuran and cooled in a dry ice-acetone bath. n-Butyllithium (14 mmol) was added and the resultant mixture stirred for 30 minutes. The mixture was then poured onto an diethyl ether—dry ice mixture and allowed to warm to ambient temperature. The mixture was then evaporated and partitioned between 5% aqueous sulfuric acid and methylene chloride. The organic layer was dried with sodium sulfate and evaporated to an oil which crystallized from ether, mp 133°–134° C. 300 MHz $^1$H NMR (DMSO-D): δ, 5.22 (d,1H,PCH). MS: 307 (—OH), 279 (—$CO_2H$).

EXAMPLE 15

O,O-Diethyl Benzoyl(1-naphthyl)methylphosphonate

O,O-Diethylphosphono-1-naphthylacetic acid (2.05 g, 6.08 mmol) was suspended in toluene (30 mL), under $N_2$, and treated with oxalyl chloride (12.2 mmol) at room temp. Dimethylformamide (0.1 mL) was added and the reaction mixture was stirred at room temp. for 20 minutes, during which all solids dissolved to give a yellow solution. The reaction mixture was concentrated to dryness to give the acid chloride product as a yellow gum which was used immediately without further purification.

O,O-Diethylphosphono-1-naphthylacetyl chloride (2.05 g, 6.08 mmol) was dissolved in tetrahydrofuran (30 mL), under $N_2$, and cooled to −78° C. (dry ice-acetone bath). Phenylmagnesium bromide (1.0M solution in tetrahydrofuran, 12.2 mL, 12.2 mmol) was added dropwise. The reaction mixture was stirred in the dry ice-acetone bath for 30 minutes and then quenched with saturated. aqueous $NH_4Cl$ (50 mL). The mixture was extracted with $CH_2Cl_2$ (2×100 mL), and the combined organic extracts were dried (MgSO₄), filtered, and concentrated to dryness to give 2.19 g of a yellow gum. The crude product was chromatographed on a silica gel column. Elution with ethyl acetate/hexane (1:1) afforded analytically pure ketone as a yellow oil which solidified to a white solid on standing, 1.11 g (47.7%), mp 119°–122° C. 300 MHz $^1$H NMR (CDCl₃): δ,6.11 (d,1H, J=21.72 Hz, PCH). MS (DCI): 383 (M+1).

EXAMPLE 16 (CP#51)

1-Benzoyl(1-Naphthyl)methylphosphonic Acid

A solution of O,O-diethyl benzoyl(1-naphthyl)methylphosphonate (1.04 g, 2.73 mmol) in CH₂Cl₂ (50 mL), under N₂, was treated with bromotrimethylsilane (2.51 g, 16.4 mmol) and the resulting solution was stirred at room temperature for 2 hours. The reaction mixture was concentrated to dryness and the residue obtained was heated in a mixture of ethanol (15 mL) and hydrochloric acid 5 mL). The mixture was then concentrated to dryness and the residue, a yellow oil, was crystallized from ethanol (15 mL)/H₂O (5 mL), filtered, washed with ethanol (5 mL), and dried to afford 649 mg (71.8%) analytically pure product as a white solid, mp 184°–187° C. 300 MHz $^1$H NMR (DMSO-D): δ, 6.23 (d,1H, J=22.79 Hz,PCH). MS: 327 (M+1), 247 [(M+2)-PO₃H₂)].

TABLE 2

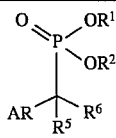

| CP # | Ex # | R¹R² | AR | R⁵ | R⁶ | Formula | MP °C. |
|---|---|---|---|---|---|---|---|
| 4 | 6 | H | Phenyl | cyclohexyl | H | C₁₃H₁₉O₃P | 155–156 |
| 5 | 10 | H | Phenyl | cycloheptyl | H | C₁₄H₂₁O₃P | 161–162 |
| 6 | 10 | H | 4-Phenylphenyl | cyclohexyl | H | C₁₉H₂₃O₃P | 156–158 |
| 7 | 10 | H | 3-CH₃-Phenyl | cyclohexyl | H | C₁₄H₂₁O₃P | 155–156 |
| 8 | 10 | H | 2-CH₃-Phenyl | cyclohexyl | H | C₁₄H₂₁O₃P | 165–166 |
| 9 | 10 | H | Phenyl | (CH₂)₂Phenyl | H | C₁₅H₁₇O₃P | 154–155 |
| 10 | 10 | H | Phenyl | (CH₂)₄Phenyl | H | C₁₇H₂₁O₃P | 128–132 |
| 11 | 4 | H | 2-CH₃-Phenyl | Phenyl | H | C₁₄H₁₅O₃P | 252–255 |
| 12 | 4 | H | 2-F-Phenyl | Phenyl | H | C₁₃H₁₂FO₃P | 198–202 |
| 13 | 4 | H | 2-Cl-Phenyl | Phenyl | H | C₁₃H₁₂ClO₃P | 237–239 |
| 14 | 4 | H | 2-CF₃-Phenyl | Phenyl | H | C₁₄H₁₂F₃O₃P | 127–130 |
| 15 | 4 | H | 3-Cl-Phenyl | Phenyl | H | C₁₃H₁₂ClO₃P | 182–183 |
| 16 | 4 | H | 3-CF₃-Phenyl | Phenyl | H | C₁₄H₁₂F₃O₃P | 173–176 |
| 17 | 4 | H | 3-NO₂-Phenyl | Phenyl | H | C₁₃H₁₂NO₅P | 194–196 |
| 18 | 4 | H | 3-CH₃-Phenyl | Phenyl | H | C₁₄H₁₅O₃P | 179–181 |
| 19 | 6 | H | 2,5-(CH₃)₂-Phenyl | Phenyl | H | C₁₅H₁₇O₃P | 204–207 |
| 20 | 8 | H | 3-CF₃-Phenyl | 3-CF₃-Phenyl | H | C₁₅H₁₁F₆O₃P | 191–193 |
| 21 | 4 | H | 4-F-Phenyl | Phenyl | H | C₁₃H₁₂FO₃P | 252–253 |
| 22 | 6 | H | 4-CH₃-Phenyl | Phenyl | H | C₁₄H₁₅O₃P | 223–225 |
| 23 | 6 | H | 4-CF₃-Phenyl | Phenyl | H | C₁₄H₁₂F₃O₃P | 219–221 |
| 24 | 6 | H | 4-OCH₃-Phenyl | Phenyl | H | C₁₄H₁₅O₄P | 199–201 |
| 25 | 10 | H | Phenyl | 4-Phenylbenzyl | H | C₂₀H₁₉O₃P | 212–215 |
| 26 | 6 | H | 4-Br-Phenyl | Phenyl | H | C₁₃H₁₂BrO₃P | 242–244 |
| 27 | 6 | H | 4-Cl-Phenyl | Phenyl | H | C₁₃H₁₂ClO₃P | 242–244 |
| 28 | 6 | H | 4-Phenylphenyl | 4-Phenylphenyl | H | C₂₅H₂₁O₃P | >320 dec |
| 29 | 10 | H | 3-CH₃-Phenyl | Benzyl | H | C₁₅H₁₇O₃P | 156–159 |
| 30 | 10 | H | 3-CH₃-Phenyl | 4-Cl-Benzyl | H | C₁₅H₁₆ClO₃P | 195–196 |
| 31 | 10 | H | 3-CF₃-Phenyl | 3-CH₃-Benzyl | H | C₁₆H₁₆F₃O₃P | 113–116 |
| 32 | 10 | H | 3-CF₃-Phenyl | 4-CF₃-Benzyl | H | C₁₆H₁₃F₆O₃P | 186–188 |
| 33 | 11 | H | Phenyl | 4-Cl-Benzyl | H | C₁₄H₁₄ClO₃P | 173–176 |
| 34 | 4 | H | Phenyl | Benzyl | H | C₁₄H₁₅O₃P | 164–166 |
| 35 | 10 | H | 3-CF₃-Phenyl | 3-CF₃-Benzyl | H | C₁₆H₁₃F₆O₃P | 88–90 |
| 36 | 10 | H | 3-CF₃-Phenyl | Benzyl | H | C₁₅H₁₄F₃O₃P | 156–159 |
| 37 | 10 | H | 3-CF₃-Phenyl | 4-F-Benzyl | H | C₁₅H₁₃F₄O₃P | 170–172 |
| 38 | 10 | H | 3-CF₃-Phenyl | 4-Phenylbenzyl | H | C₂₁H₁₈F₃O₃P | 192–195 |
| 39 | 6 | H | 1-Naphthyl | COOH | H | C₁₂H₁₁O₅P | 195 |
| 40 | 11 | H | 2-Naphthyl | Benzyl | H | C₁₈H₁₇O₃P | 190–191 |
| 41 | 11 | H | 1-Naphthyl | cyclohexyl | H | C₁₈H₂₃O₃P | 154–157 |
| 42 | 11 | H | 1-Naphthyl | 4-Phenylbenzyl | H | C₂₄H₂₁O₃P | 196–199 |
| 43 | 11 | H | 6-(CH₃)-1-naphthyl | CH₂cyclohexyl | H | C₁₉H₂₅O₃P | 257–259 |
| 44 | 11 | H | 1-Naphthyl | 4-OCH₃-Benzyl | H | C₁₉H₁₉O₄P | 170–176 |
| 45 | 11 | H | 1-Naphthyl | Benzyl | H | C₁₈H₁₇O₃P | 73–77 |
| 46 | 11 | H | 1-Naphthyl | 4-CH₃-Benzyl | H | C₁₉H₁₉O₃P | 198–203 |
| 47 | 11 | H | 1-Naphthyl | 4-NO₂-Benzyl | H | C₁₈H₁₆NO₅P | 197–215 dec |
| 48 | 11 | H | 1-Naphthyl | 4-Cl-Benzyl | H | C₁₈H₁₆ClO₃P | 204–206 |
| 49 | 12 | H | 1-Naphthyl | 4-Cl-Benzyl | 4-Cl-Benzyl | C₂₅H₂₁Cl₂O₃P | 142–145 |
| 50 | 16 | H | 1-Naphthyl | 4-Phenylbenzoyl | H | C₂₄H₁₉O₄P | 200–208 dec |
| 51 | 16 | H | 1-Naphthyl | Benzoyl | H | C₁₈H₁₅O₄P | 184–187 |
| 52 | 16 | H | 1-Naphthyl | 1-Naphthoyl | H | C₂₂H₁₇O₄P | 201–204 dec |
| 53 | 16 | H | 1-Naphthyl | 2-Naphthoyl | H | C₂₂H₁₇O₄P | 185–190 |
| 54 | 16 | H | 1-Naphthyl | COcyclohexyl | H | C₁₈H₂₁O₄P | 170–172 |

TABLE 2-continued

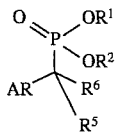

| CP # | Ex # | $R^1R^2$ | AR | $R^5$ | $R^6$ | Formula | MP °C. |
|---|---|---|---|---|---|---|---|
| 55 | 13 | H | 1-Naphthyl | Benzoyl | Benzoyl | $C_{25}H_{19}O_5P$ | 153–155 |
| 56 | 9 | Ethyl | 3-$CF_3$-Phenyl | 4-$CF_3$-Benzyl | H | $C_{20}H_{21}F_6O_3P$ | OIL |
| 57 | 9 | Ethyl | 3-$CF_3$-Phenyl | 3-$CF_3$-Benzyl | H | $C_{20}H_{21}F_6O_3P$ | OIL |
| 58 | 9 | Ethyl | Phenyl | 4-Cl-Benzyl | H | $C_{18}H_{22}ClO_3P$ | OIL |
| 59 | 14 | Ethyl | 1-Naphthyl | COOH | H | $C_{16}H_{19}O_5P$ | 133–134 |
| 60 | 9 | Ethyl | Phenyl | 4-Phenylbenzyl | H | $C_{24}H_{27}O_3P$ | 61–63 |
| 61 | 11 | Ethyl | 1-Naphthyl | 4-Cl-Benzyl | H | $C_{22}H_{24}ClO_3P$ | OIL |
| 62 | 11 | Ethyl | 1-Naphthyl | Benzyl | H | $C_{22}H_{25}O_3P$ | OIL |
| 63 | 5 | Ethyl | 3-$CH_3$-Phenyl | Phenyl | H | $C_{18}H_{23}O_3P$ | OIL |
| 64 | 5 | Ethyl | 4-F-Phenyl | Phenyl | H | $C_{17}H_{20}FO_3P$ | OIL |
| 65 | 5 | Ethyl | 3-Cl-Phenyl | Phenyl | H | $C_{17}H_{20}ClO_3P$ | OIL |
| 66 | 9 | Ethyl | Phenyl | $(CH_2)_4$Phenyl | H | $C_{21}H_{29}O_3P$ | OIL |
| 67 | 9 | Ethyl | 3-$CH_3$-Phenyl | Benzyl | H | $C_{19}H_{25}O_3P$ | OIL |
| 68 | 9 | Ethyl | 3-$CH_3$-Phenyl | 4-Cl-Benzyl | H | $C_{19}H_{24}ClO_3P$ | OIL |
| 69 | 5 | Ethyl | 2-$CH_3$-Phenyl | Phenyl | H | $C_{18}H_{23}O_3P$ | OIL |
| 70 | 5 | Ethyl | 4-$NO_2$-Phenyl | Phenyl | H | $C_{17}H_{20}NO_5P$ | OIL |
| 71 | 5 | Ethyl | 4-$CH_3$-Phenyl | Phenyl | H | $C_{18}H_{23}O_3P$ | 62–64 |
| 72 | 5 | Ethyl | 2-F-Phenyl | Phenyl | H | $C_{17}H_{20}FO_3P$ | OIL |
| 73 | 5 | Ethyl | 4-$CF_3$-Phenyl | Phenyl | H | $C_{18}H_{20}F_3O_3P$ | OIL |
| 74 | 5 | Ethyl | 3-$NO_2$-Phenyl | Phenyl | H | $C_{17}H_{20}NO_5P$ | OIL |
| 75 | 5 | Ethyl | 4-Br-Phenyl | Phenyl | H | $C_{17}H_{20}BrO_3P$ | 62–64 |
| 76 | 5 | Ethyl | 2-Cl-Phenyl | Phenyl | H | $C_{17}H_{20}ClO_3P$ | OIL |
| 77 | 5 | Ethyl | 4-Cl-Phenyl | Phenyl | H | $C_{17}H_{20}ClO_3P$ | 52–54 |
| 78 | 5 | Ethyl | 3-$CF_3$-Phenyl | Phenyl | H | $C_{18}H_{20}F_3O_3P$ | 67–69 |
| 79 | 5 | Ethyl | 2,5-$(CH_3)_2$-Phenyl | Phenyl | H | $C_{19}H_{25}O_3P$ | OIL |
| 80 | 9 | Ethyl | 3-$CF_3$-Phenyl | 3-$CH_3$-Benzyl | H | $C_{20}H_{24}F_3O_3P$ | OIL |
| 81 | 9 | Ethyl | 3-$CF_3$-Phenyl | 3-Cl-Benzyl | H | $C_{19}H_{21}ClF_3O_3P$ | OIL |
| 82 | 5 | Ethyl | 3-$OCH_3$-Phenyl | Phenyl | H | $C_{18}H_{23}O_4P$ | OIL |
| 83 | 7 | Ethyl | 3-$CF_3$-Phenyl | 3-$CF_3$-Phenyl | H | $C_{19}H_{19}F_6O_3P$ | 82–85 |
| 84 | 9 | Ethyl | Phenyl | Phenylpropyl | H | $C_{20}H_{27}O_3P$ | OIL |
| 85 | 9 | Ethyl | Phenyl | Phenylethyl | H | $C_{19}H_{25}O_3P$ | OIL |
| 86 | 9 | Ethyl | 3-$CF_3$-Phenyl | 4-F-Benzyl | H | $C_{19}H_{21}F_4O_3P$ | OIL |
| 87 | 9 | Ethyl | 3-$CF_3$-Phenyl | 4-$OCH_3$-Benzyl | H | $C_{20}H_{24}F_3O_4P$ | OIL |
| 88 | 5 | Ethyl | Phenyl | cyclohexyl | H | $C_{17}H_{27}O_3P$ | OIL |
| 89 | 5 | Ethyl | 4-Phenylphenyl | 4-Phenylphenyl | H | $C_{29}H_{29}O_3P$ | 163–165 |
| 90 | 9 | Ethyl | 3-$CF_3$-Phenyl | Benzyl | H | $C_{19}H_{22}F_3O_3P$ | OIL |
| 91 | 9 | Ethyl | 3 $CH_3$-Phenyl | cyclohexyl | H | $C_{18}H_{29}O_3P$ | OIL |

We claim:

1. A compound represented by the general formula I:

I wherein $R^1$ and $R^2$ are the same or different and are selected from any of H, $C_1$-$C_4$ alkyl, $C_1$-$C_4$ alkylsulfonyl, $C_1$-$C_4$ alkyl $NR^3R^4$ wherein $R^3$ and $R^4$ are the same or different and selected from either $C_1$-$C_4$ alkyl or H, or aralkyl wherein the alkyl portion has 1 carbon atom and the aryl portion is optionally independently substituted with any of halo, nitro, $C_1$-$C_2$ alkyl or methylsulfonyl;

wherein AR is selected from any of aryl or substituted aryl wherein the substituents are independently selected from any of $C_1$-$C_4$ alkoxy, $C_1$-$C_8$ alkyl, cyano, halo, hydroxy, nitro, phenoxy, phenyl, or trifluoromethyl;

wherein $R^5$ is independently selected from any of carboxyl, $C_3$-$C_7$ cycloalkyl, aryl, COaryl, COalkyl, COcycloalkyl, or aralkyl, wherein aryl is phenyl, naphthyl or substituted aryl wherein the substituents are independently selected from any of amino, acylamino, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl or trifluoromethyl;

wherein $R^6$ is selected from any of hydrogen, carboxy, carboalkoxy, $C_3$-$C_7$ cycloalkyl, aryl, COaryl, COalkyl, COcycloalky ($C_3$-$C_7$), or aralkyl, where aryl is phenyl, naphthyl or substituted aryl wherein the substituents are independently selected from any of amino, acylamino, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl, or trifluoromethyl;

or the optical isomers, enantiomers, diastereomers, or pharmaceutically acceptable salts thereof:

with the proviso the following compounds are excluded from the definition of formula I;

a) $R^1R^2$ are alkyl, AR is phenyl or phenyl substituted by halo, alkoxy, alkyl, trifluoromethyl, $R^5$ is carboxyl, phenyl, 1-naphthyl, substituted phenyl, 1-(4-$NO_2$)-naphthyl, cyclopentyl or cyclohexyl, $(CH2)_n$Aryl where aryl is phenyl and n=1 or 2, and $R^6$=hydrogen and b) $R^1R^2$ is hydrogen, AR is phenyl, $R^5$ is carboxyl, phenyl or $(CH2)n$Aryl where Aryl is phenyl and n=1 or 2, and $R^6$ is hydrogen.

2. The compound of claim 1, wherein $R^1$ and $R^2$ are both H.

3. The compound of claim 1, wherein the substituents of AR are independently selected from any of $C_1$-$C_8$ alkyl, halo, trifluoromethyl.

4. The compound of claim 3, wherein AR is naphthyl.

5. The compound of claim 1, wherein $R^5$ is aryl, $C_3$-$C_7$ cycloalkyl, or substituted aryl wherein the substituents are independently selected from any of $C_1$-$C_8$ alkyl or $C_1$-$C_4$ alkoxy, halogen, or trifluoromethyl.

6. The compound of claim 5, wherein the $R^5$ is trifluoromethylphenyl.

7. The compound of claim 5, wherein $R^5$ is cyclohexyl.

8. The compound of claim 5, wherein $R^5$ is benzyl.

9. The compound of claim 1, wherein $R^5$ is COaryl and aryl is selected from any of phenyl, or substituted phenyl wherein the substituents are independently selected from any of $C_1$-$C_8$ alkyl, halo, phenyl, or trifluoromethyl.

10. The compound of claim 1, wherein $R^6$ is $(CH2)_n$-aryl and n is 1 to 2.

11. The compound of claim 1 wherein $R^6$ is COaryl and aryl is selected from any of phenyl, or substituted phenyl wherein the substituents are independently selected from any of $C_1$-$C_8$ alkyl, halo, phenyl, or trifluoromethyl.

12. The compound of claim 1 wherein $R^5$ and $R^6$ are both COaryl or $(CH_2)_n$-aryl.

13. The compound of claim 1 selected from any of:
2-Trifluoromethylphenyl(phenyl)methylphosphonic acid;
2,5-Dimethylphenyl(phenyl)methylphosphonic acid;
3-Trifluoromethylphenyl(3-trifluoromethylphenyl)methylphosphonic acid;
3-Trifluoromethylphenyl(3-trifluoromethylbenzyl)methylphosphonic acid;
4-Chlorophenyl(1-naphthyl)methylphosphonic acid;
O,O-Diethyl bis(4-chlorobenzyl)(1-naphthyl)methylphosphonate;
bis(4-Chlorobenzyl)(1-naphthyl)methylphosphonic acid;
O,O-Diethyl benzoyl(1-naphthyl)methylphosphonate; or
Benzoyl(1-naphthyl)methylphosphonic acid.

14. The compound of claim 13, selected from any of:
2-Trifluoromethylphenyl(phenyl)methylphosphonic acid;
2,5-Dimethylphenyl(phenyl)methylphosphonic acid;
3-Trifluoromethylphenyl(3-trifluoromethylphenyl)methylphosphonic acid;
3-Trifluoromethylphenyl(4-trifluoromethylbenzyl)methylphosphonic acid;
4-Chlorophenyl(1-naphthyl)methylphosphonic acid;
bis(4-Chlorobenzyl)(1-naphthyl)methylphosphonic acid or
Benzoyl(1-naphthyl)methylphosphonic acid.

15. A pharmaceutical composition comprising the compound represented by the general formula I:

wherein $R^1$ and $R^2$ are the same or different and are selected from any of H, $C_1$-$C_4$ alkyl, $C_1$-$C_4$ alkylsulfonyl, $C_1$-$C_4$ alkyl $NR^3R^4$ wherein $R^3$ and $R^4$ are the same or different and selected from either $C_1$-$C_4$ alkyl or H, or aralkyl wherein the alkyl portion has 1 carbon atom and the aryl portion is optionally independently substituted with any of halo, nitro, $C_1$-$C_2$ alkyl or methylsulfonyl;

wherein AR is selected from any of aryl or substituted aryl wherein the substituents are independently selected from any of $C_1$-$C_4$ alkoxy, $C_1$-$C_8$ alkyl, cyano, halo, hydroxy, nitro, phenoxy, phenyl, or trifluoromethyl;

wherein $R^5$ is independently selected from any of carboxyl, $C_3$-$C_7$ cycloalkyl, aryl, COaryl, COalkyl, COcycloalkyl, or aralkyl, wherein aryl is phenyl, naphthyl or substituted aryl wherein the substituents are independently selected from any of amino, acylamino, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl nitro, phenoxy, phenyl or trifluoromethyl;

wherein $R^6$ is selected from any of hydrogen, carboxy, carboalkoxy, $C_3$-$C_7$ cycloalkyl, aryl, COaryl, COalkyl, COcycloalky ($C_3$-$C_7$), or aralkyl, where aryl is phenyl, naphthyl or substituted aryl wherein the substituents are independently selected from any of amino, acylamino, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl, or trifluoromethyl;

or the optical isomers, enantiomers, diastereomers, or pharmaceutically acceptable salts thereof, in combination with a pharmaceutically acceptable carrier, said compound being present in a therapeutically effective amount for treating a bone wasting disease.

16. A method of treating a bone wasting disease comprising administering the compound represented by the general formula I:

wherein $R^1$ and $R^2$ are the same or different and are selected from any of H, $C_1$-$C_4$ alkyl, $C_1$-$C_4$ alkylsulfonyl, $C_1$-$C_4$ alkyl $NR^3R^4$ wherein $R^3$ and $R^4$ are the same or different and selected from either $C_1$-$C_4$ alkyl or H, or aralkyl wherein the alkyl portion has 1 carbon atom and the aryl portion is optionally independently substituted with any of halo, nitro, $C_1$-$C_2$ alkyl or methylsulfonyl;

wherein AR is selected from any of aryl or substituted aryl wherein the substituents are independently selected from any of $C_1$-$C_4$ alkoxy, $C_1$-$C_8$ alkyl, cyano, halo, hydroxy, nitro, phenoxy, phenyl, or trifluoromethyl;

wherein $R^5$ is independently selected from any of carboxyl, $C_3$-$C_7$ cycloalkyl, aryl, COaryl, COalkyl, COcycloalkyl, or aralkyl, wherein aryl is phenyl, naphthyl or substituted aryl wherein the substituents are independently selected from any of amino, acylamino, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl or trifluoromethyl;

wherein $R^6$ is selected from any of hydrogen, carboxy, carboalkoxy, $C_3$-$C_7$ cycloalkyl, aryl, COaryl, COalkyl, COcycloalky ($C_3$-$C_7$), or aralkyl, where aryl is phenyl, naphthyl or substituted aryl wherein the substituents are independently selected from any of amino, acylamino, $C_1$-$C_4$ alkoxy, $C_1$-$C_8$ alkyl, carboxy, $C_1$-$C_4$ carboalkoxy, cyano, halo, hydroxy, methylsulfonamido, methylsulfonyl, phenylsulfonamido, phenylsulfonyl, nitro, phenoxy, phenyl, or trifluoromethyl;

or the optical isomers, enantiomers, diastereomers, or pharmaceutically acceptable salts thereof, to an animal afflicted with said disease in an amount effective for treating the bone wasting disease.

17. The method of claim 16, wherein the compound is 3-Trifluoromethylphenyl(3-trifluoromethylphenyl)methylphosphonic acid.

18. The method of claim 16, wherein the effective amount is 0.001–50 mg/kg.

19. The method of claim 16, wherein the disease is osteoporosis.

* * * * *